United States Patent
McPeak et al.

(10) Patent No.: US 10,213,581 B2
(45) Date of Patent: Feb. 26, 2019

(54) DIRECTIONAL SUBINTIMAL ACCESS FOR CHEMICAL AGENT DELIVERY

(71) Applicant: COVIDIEN LP, Mansfield, MA (US)

(72) Inventors: Thomas McPeak, Shakopee, MN (US); William Whealon, Chaska, MN (US)

(73) Assignee: Covidien LP, Mansfield, MA (US)

( * ) Notice: Subject to any disclaimer, the term of this patent is extended or adjusted under 35 U.S.C. 154(b) by 873 days.

(21) Appl. No.: 14/162,945

(22) Filed: Jan. 24, 2014

(65) Prior Publication Data

US 2015/0209548 A1    Jul. 30, 2015

(51) Int. Cl.
| | | |
|---|---|---|
| A61M 25/00 | (2006.01) | |
| A61M 25/06 | (2006.01) | |
| A61M 37/00 | (2006.01) | |

(52) U.S. Cl.
CPC .... *A61M 25/0054* (2013.01); *A61M 25/0082* (2013.01); *A61M 25/0662* (2013.01); *A61M 37/0069* (2013.01); *A61M 25/007* (2013.01); *A61M 2025/0095* (2013.01); *A61M 2025/0681* (2013.01); *A61M 2202/0468* (2013.01); *A61M 2210/12* (2013.01)

(58) Field of Classification Search
CPC .......... A61M 37/0069; A61M 25/0054; A61M 2025/0056; A61M 2025/105; A61M 2025/1086; A61M 25/104; A61M 25/0662; A61F 2/915
See application file for complete search history.

(56) References Cited

U.S. PATENT DOCUMENTS

| | | | |
|---|---|---|---|
| 4,697,575 A | * 10/1987 | Horowitz | .......... A61M 37/0069 600/8 |
| 4,936,823 A | * 6/1990 | Colvin | ...................... A61F 2/01 600/7 |
| 5,017,381 A | 5/1991 | Maruyama et al. | |
| 5,312,456 A | * 5/1994 | Reed | ........................ A61F 2/82 24/442 |
| 6,273,851 B1 | * 8/2001 | Slater | ................... A61N 5/1027 600/3 |
| 7,736,292 B2 | * 6/2010 | Hermann | ............. A61N 5/1007 600/3 |

(Continued)

FOREIGN PATENT DOCUMENTS

| | | |
|---|---|---|
| EP | 0292630 B1 | 3/1995 |
| EP | 2343100 B1 | 9/2012 |

OTHER PUBLICATIONS

Vertellus Biomaterials—Biocompatible Polymer Coatings for Drug Delivery. Retrieved from the Internet URL: http://www.pharmaceutical-technology.com/contractors/materials/vertellus.

(Continued)

*Primary Examiner* — Nathan R Price
*Assistant Examiner* — Melissa A Snyder
(74) *Attorney, Agent, or Firm* — Shumaker & Sieffert, P.A.

(57) ABSTRACT

Various devices, systems, and methodologies are disclosed for delivering a chemical agent to tissue, e.g., for delivering an anti-restenotic agent to tissue comprising a wall of a blood vessel. In one embodiment of the disclosure, a delivery member is disclosed comprising a body that includes a plurality of discrete, separable sections, wherein each section includes a housing defining an internal cavity, and a penetrating member that extends from the housing.

28 Claims, 15 Drawing Sheets

(56) References Cited

U.S. PATENT DOCUMENTS

| | | | |
|---|---|---|---|
| 7,955,382 B2* | 6/2011 | Flanagan | A61F 2/82 623/1.42 |
| 2004/0158118 A1 | 8/2004 | Drobnik et al. | |
| 2009/0196903 A1 | 8/2009 | Kliman | |
| 2010/0298698 A1 | 11/2010 | Burbank et al. | |
| 2012/0041412 A1* | 2/2012 | Roth | A61M 25/10 604/500 |
| 2012/0130339 A1 | 5/2012 | Farra | |
| 2013/0296917 A1 | 11/2013 | Rees | |
| 2013/0331818 A1 | 12/2013 | Buysman et al. | |
| 2014/0364935 A1* | 12/2014 | Eli | A61F 2/91 623/1.12 |

OTHER PUBLICATIONS

Wilensky et al. Progress in Cardiology. American Heart Journal. "Direct intraarterial wall injection of microparticles via a catheter: A potential drug delivery strategy following angioplasty" Oct. 1991, vol. 122, pp. 1136-1140.

International Search Report and Written Opinion from counterpart International Patent Application No. PCT/US2015/010804, dated Apr. 23, 2015, 16 pp.

Notice of Reasons for Rejection, and English translation thereof, from counterpart Japanese Application No. 2016-547905, dated Sep. 27, 2018, 16 pp.

* cited by examiner

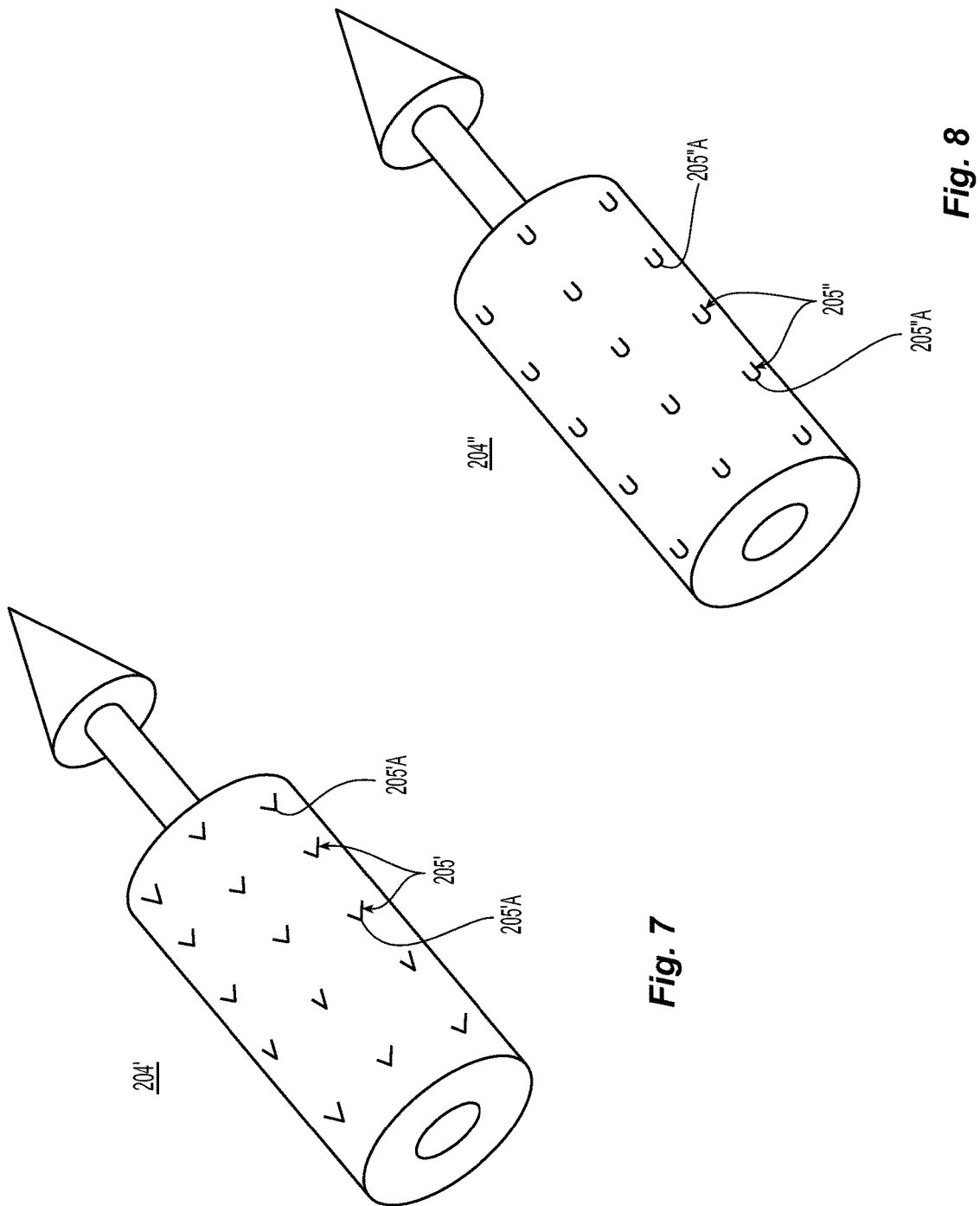

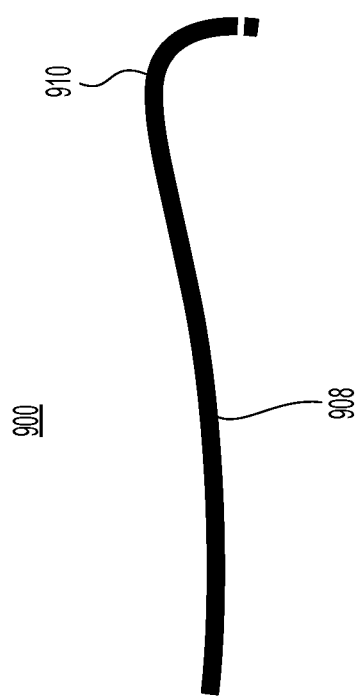

DIRECTIONAL SUBINTIMAL ACCESS FOR CHEMICAL AGENT DELIVERY

TECHNICAL FIELD

The present disclosure generally relates to the treatment and prevention of occlusions within tubular organs, and more specifically, to the delivery of chemical agent(s) to vascular tissue to inhibit restenosis.

BACKGROUND

Restenosis, or the re-narrowing of a blood vessel, is not an uncommon occurrence following the treatment of an initial vascular occlusion, and may lead to restricted blood flow within the blood vessel. Known techniques for inhibiting the formation of vascular occlusions include the delivery of anti-restenotic agents, and typically involve the placement of an implanted device within the lumen of a blood vessel to do so. For example, a stent, or other such structure, may be coated with the anti-restenotic agent, and implanted within the lumen of the vessel such that the anti-restenotic agent is eluted into the tissue comprising the wall of the vessel over time. Such techniques and structures, however, typically deliver the anti-restenotic agent to the intimal layer of the vessel wall along the entire periphery of the vessel wall, and are limited in their efficacy due to the nature of the tissue comprising the intimal layer.

Consequently, there remains a need for devices, systems, and methodologies that facilitate directional, targeted delivery of an anti-restenotic agent in a more efficacious manner.

SUMMARY

In one aspect of the present disclosure, a delivery member is disclosed for use in delivering a chemical agent to tissue. The delivery member includes a body including a plurality of discrete, separable sections, which may be identical in configuration. Each section of the body includes a housing defining an internal cavity, and a penetrating member that extends from the housing.

The housing includes first and second opposing ends. The first end of the housing includes an opening, and the penetrating member extends from the second end. The penetrating member is configured to facilitate passage of the delivery member through the tissue, and may be incisive in configuration.

The plurality of sections are configured and dimensioned such that an applied tensile force separates adjacent sections. In some embodiments of the delivery member, the plurality of sections includes a first section with a first housing having an opening formed therein, and a first penetrating member extending from the first housing, as well as a second section with a second housing having an opening formed therein, and a second penetrating member extending from the second housing. In such embodiments, the first penetrating member is positioned within the second housing, and the opening in the second housing defines a transverse cross-sectional dimension smaller than a maximum transverse cross-sectional dimension defined by the first penetrating member. The first and second sections may be formed from a resilient material such that a tensile force applied to the delivery member causes the first penetrating member and/or the opening in the second housing to deform, and thereby permit the first penetrating member to be withdrawn from the second housing to separate the first and second sections.

In some embodiments of the delivery member, the plurality of sections further includes a third section with a third housing having an opening formed therein, and a third penetrating member extending from the third housing, and a fourth section with a fourth housing having an opening formed therein, and a fourth penetrating member extending from the fourth housing. In such embodiments, the third penetrating member is positioned within the fourth housing, and the opening in the fourth housing defines a transverse cross-sectional dimension smaller than a maximum transverse cross-sectional dimension defined by the third penetrating member. The third and fourth sections may be formed from a resilient material such that the tensile force applied to the delivery member causes the third penetrating member and/or the opening in the fourth housing to deform, and thereby permit the third penetrating member to be withdrawn from the fourth housing to separate the third and fourth sections. Depending upon the location to be treated in the body additional sections may be included to form a delivery member of an appropriate length.

In another aspect of the present disclosure, a system is disclosed for use in treating a blood vessel that includes a guide catheter that is insertable into a lumen of the blood vessel, and a delivery member.

The guide catheter defines an internal passageway, and the delivery member is insertable into the internal passageway of the guide catheter. The delivery member includes a plurality of discrete, separable sections, each of which includes an anti-restenotic agent, and may be identical in configuration.

Each section includes a housing that defines an internal cavity, as well as a penetrating member extending from the housing that is configured to facilitate passage of the delivery member through tissue, e.g., a wall of the blood vessel.

The plurality of sections are configured and dimensioned such that a tensile force applied to the delivery member separates adjacent sections.

In some embodiments of the system, the plurality of sections of the delivery member includes a first section with a first housing having an opening formed therein, and a first penetrating member extending from the first housing, and a second section with a second housing having an opening formed therein, and a second penetrating member extending from the second housing. In such embodiments, the first penetrating member is positioned within the second housing, and the opening in the second housing defines a transverse cross-sectional dimension smaller than a maximum transverse cross-sectional dimension defined by the first penetrating member. The first and second sections may be formed from a resilient material such that a tensile force applied to the delivery member causes the first penetrating member and/or the opening in the second housing to deform, and thereby permit the first penetrating member to be withdrawn from the second housing to separate the first and second sections.

In additional embodiments of the system, the plurality of sections of the delivery member further includes a third section with a third housing having an opening formed therein, and a third penetrating member extending from the third housing, and a fourth section with a fourth housing having an opening formed therein, and a fourth penetrating member extending from the fourth housing. In such embodiments, the third penetrating member is positioned within the fourth housing, and the opening in the fourth housing defines a transverse cross-sectional dimension smaller than a maximum transverse cross-sectional dimension defined by the third penetrating member. The third and fourth sections may be formed from a resilient material such that the tensile force applied to the delivery member causes the third penetrating member and/or the opening in the fourth housing to deform, and thereby permit the third penetrating member to be withdrawn from the fourth housing to separate the third and fourth sections.

In another aspect of the present disclosure, a method of performing an endovascular procedure is disclosed that includes inserting a guide catheter into a lumen of a blood vessel, advancing a delivery member through the guide catheter, deploying the delivery member from the guide catheter such that the delivery member is positioned between adjacent tissue layers forming a wall of the blood vessel, and delivering a chemical agent between the adjacent tissue layers forming the wall of the blood vessel.

In some embodiments of the method, delivering the chemical agent includes depositing a portion of the delivery member between the adjacent tissue layers, e.g., by separating a first section of the delivery member from a second section of the delivery member, and withdrawing a remaining portion of the delivery member from the blood vessel. In such embodiments, the portion of the delivery member deposited between the adjacent tissue layers forming the wall of the blood vessel will degrade over time, whereby the chemical agent is released into the tissue of the blood vessel.

In some embodiments of the method, delivering the chemical agent includes communicating the chemical agent into an internal channel extending through the delivery member, and through a plurality of radial openings formed in the delivery member that are in communication with the internal channel. Additionally, or alternatively, the chemical agent may be delivered through an open distal end of the delivery member.

In some embodiments of the method, delivering the chemical agent includes delivering first and second compounds into the internal channel extending through the delivery member, wherein at least one of the first and second compounds includes the chemical agent. When brought into contact with each other, the first and second compounds combine to form a solid, biodegradable filament that is positioned between the adjacent tissue layers forming the wall of the blood vessel.

Other aspects, features, and advantages of the presently disclosed subject matter will be apparent from the description, the drawings, and the claims.

BRIEF DESCRIPTION OF THE DRAWINGS

FIG. 7 is a rear, perspective view illustrating a section of the delivery member according to an alternate embodiment of the disclosure;

FIG. 8 is a rear, perspective view illustrating a section of the delivery member according to an alternate embodiment of the disclosure;

FIG. 17 is a side view illustrating another embodiment of the guide catheter.

DETAILED DESCRIPTION

Figure 1:
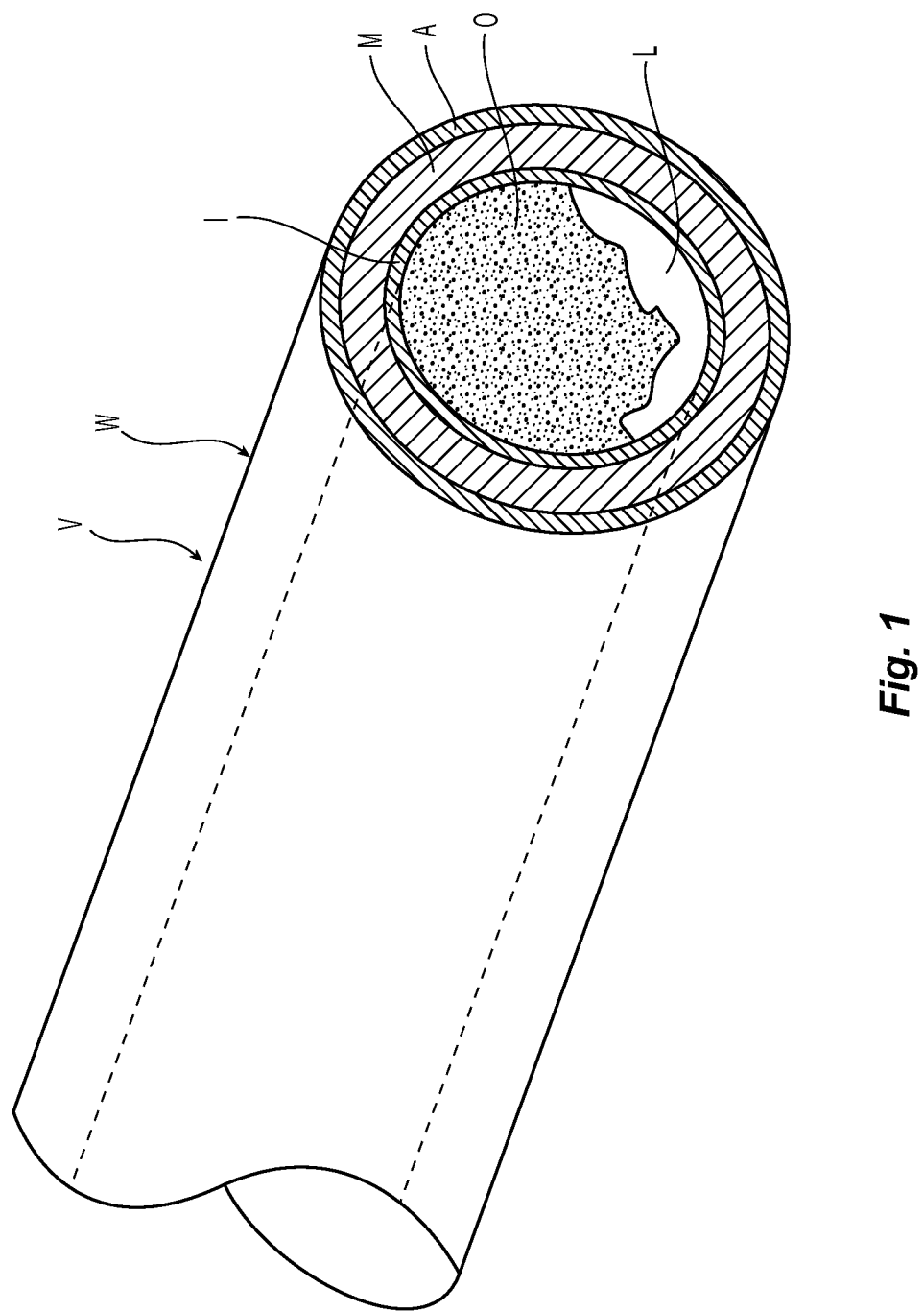
FIG. 1 is a partial cross-sectional illustration of an exemplary blood vessel.

Embodiments of the present disclosure will now be described in detail with reference to the drawings, wherein like reference numerals identify similar or identical elements. As used herein, the term "patient" refers to a human or animal patient, and the term "clinician" refers to a doctor, nurse, support personnel, or other care provider. Additionally, use of the term "occlusion" herein refers to any partial or total blockage of a hollow anatomical structure, e.g., a tubular organ, such as a blood vessel. While the devices, systems, and methodologies described herein are discussed in the context of a vascular procedure, the principles of the present disclosure are equally applicable to other surgical procedures concerning the treatment of a hollow anatomical structure. Examples of such procedures include, but are not limited to, cardiac procedures, abdominal procedures, urinary procedures, and intestinal procedures.

FIG. 1 provides a cross-sectional illustration of a blood vessel V that is obstructed by an occlusion O. The blood vessel V includes a lumen L defined by a vessel wall W that is comprised of an intimal layer I, a medial layer M, and an adventitial layer A.

Figure 2:
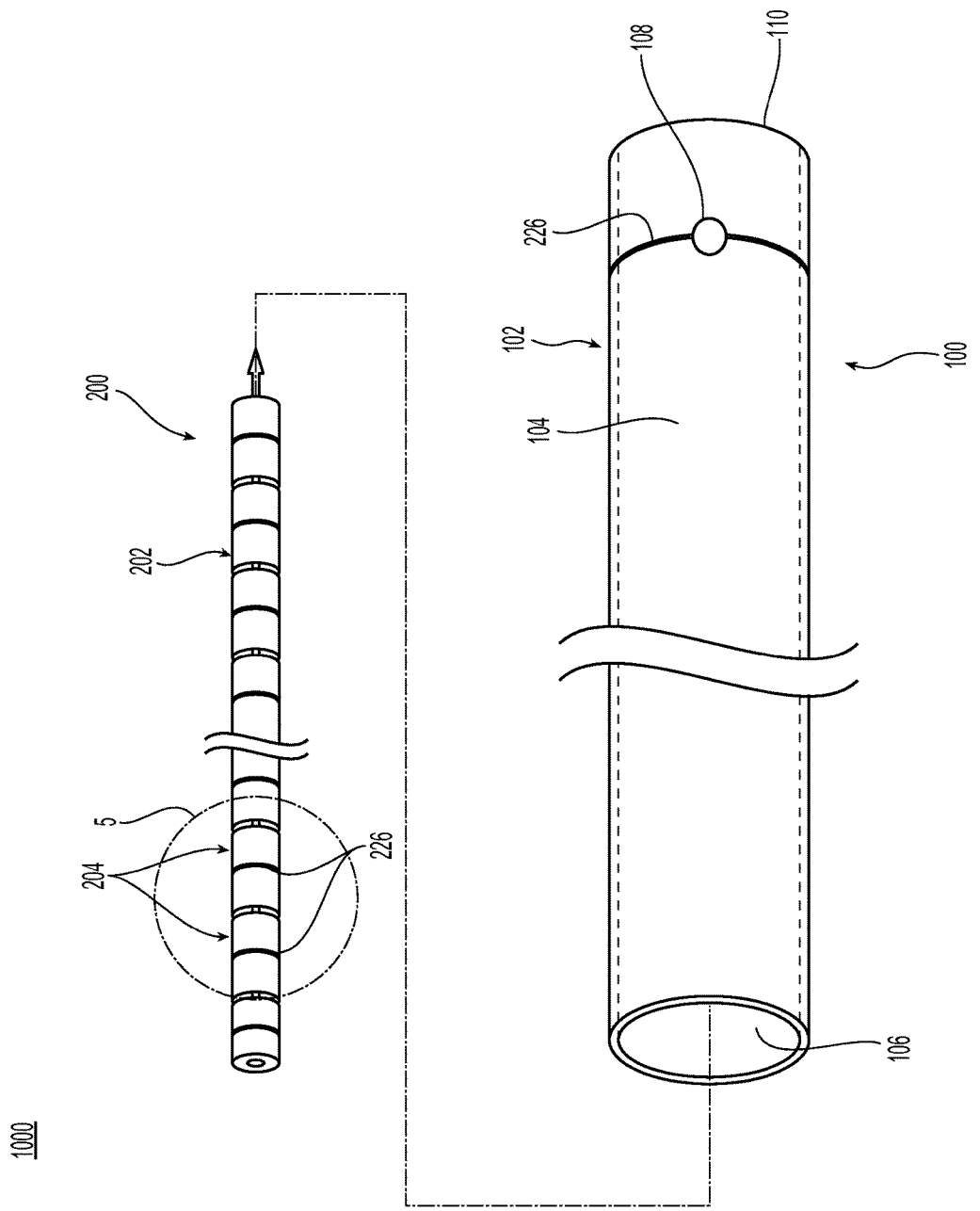
FIG. 2 illustrates a system for use in treating a blood vessel that includes a guide catheter, and a delivery member including a plurality of discrete, separable sections that is insertable into the guide catheter.
Figure 3:
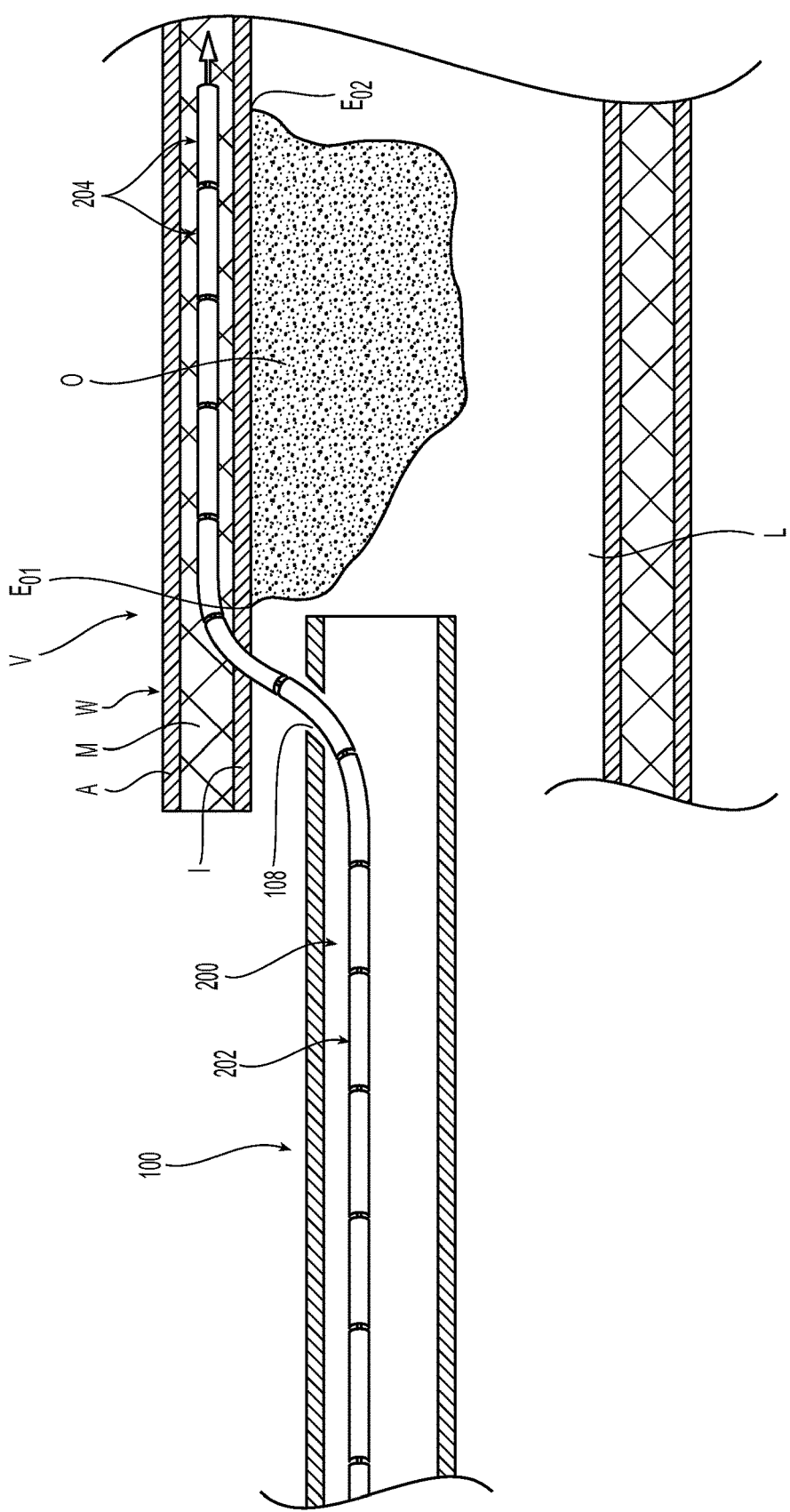
FIG. 3 is a partial longitudinal, cross-sectional view illustrating the guide catheter positioned within the blood vessel, and the delivery member positioned within the guide catheter, during the course of a surgical procedure.

FIGS. 2 and 3 illustrate a system 1000 (FIG. 2) for use in an exemplary medical procedure in which a chemical agent is delivered to the tissue forming the vessel wall W (FIGS. 1, 3) of the blood vessel V. The system 1000 includes a guide catheter 100, and a delivery member 200 that is insertable into, and movable through, the guide catheter 100.

During use of the system 1000, the guide catheter 100 is inserted into the lumen L of the blood vessel V, and is advanced through the lumen L until the guide catheter 100 is positioned proximate to the occlusion O. The delivery member 200 is then advanced through the guide catheter 100 into the tissue comprising the vessel wall W to facilitate the delivery of the chemical agent. Suitable chemical agents include anti-restenotic agents, such as, for example, paclitaxel, sirolimus, and/or a cholesterol degrading enzyme. Specifically, during deployment of the delivery member 200, the delivery member 200 is advanced from the guide catheter 100, and passed through the intimal layer I of the vessel wall W into the subintimal space, i.e., the tissue beneath the intimal layer I. More specifically, the delivery member 200 is inserted into the tissue comprising the medial layer M.

By delivering the chemical agent directly to the smooth muscle cells comprising the medial layer M, the efficacy of the chemical agent can be increased compared to the efficacy achieved in other delivery locations, e.g., the intimal layer I. The efficacy of the chemical agent, and the procedure as a whole, is further increased by the directional delivery facilitated by the guide catheter 100, which allows a specific area or section of the vessel wall W to be treated, e.g., the section of the vessel wall W immediately adjacent the occlusion O, rather than the entire circumference of the vessel wall W.

With reference now to FIGS. 1-5, the guide catheter 100 and the delivery member 200 will be discussed in detail.

The guide catheter 100 is configured and dimensioned for insertion into the lumen L (FIG. 1) of the vessel V in order to facilitate advancement, and placement, of the delivery member 200. One example of a suitable guide catheter 100 is the ECHELON™ Micro Catheter, which is made available by Covidien.

The guide catheter 100 includes a body 102 (FIG. 2) with a tubular wall 104 defining an internal passageway 106 that is configured and dimensioned to accommodate insertion and movement of the delivery member 200 therethrough. A port 108 is formed in the body 102, and is dimensioned to permit the delivery member 200 to exit the passageway 106 therethrough in order to facilitate directional deployment of the delivery member 200. Specifically, via axial and rotational manipulation of the guide catheter 100, the orientation of the port 108, and thus, deployment of the delivery member 200, can be regulated by the clinician in order to permit the delivery member to enter the tissue comprising the vessel wall W (FIGS. 1, 3) in a precise location. While the port 108 is illustrated as extending radially through the wall 104 in FIGS. 2 and 3, the port 108 may be formed at a distal end 110 of the guide catheter 100, and extend outwardly therefrom towards the occlusion O, without departing from the scope of the present disclosure. Additionally, although illustrated as including a single port 108 only, alternate configurations of the guide catheter 100 may include one or more additional ports 108.

The delivery member 200 (FIGS. 2, 3) includes a body 202 that is configured and dimensioned for insertion into, and movement through, the internal passageway 106 of the guide catheter 100. The body 202 includes a plurality of individual sections 204 that are separable from one another in a manner discussed below. In FIGS. 2 and 3, the sections 204 are illustrated as forming the entirety of the body 202 of the delivery member 200. In alternate configurations of the delivery member 200, however, the sections 204 may form only a portion of the body 202 of the delivery member 200, e.g., an end portion of the body 202.

The sections 204 (FIG. 4) are formed from a material that is at least partially resilient, such as, for example, silicone and/or fabric materials, or a synthetic resin, for example, polyurethane, polyethylene, polypropylene, nylons, polytetrafluoroethylene (PTFE), polyether ether ketone (PEEK), polyimide, combinations thereof, and the like, or from a non-biodegradable material, such as polyesters, e.g., polyalkyl terephthalates, polyamides, e.g., nylon, polyurethanes, polycarbonates, fluorooplymers, polyolefins, vinyl polymers, combinations thereof, and the like. The sections 204 may be formed through any suitable method of manufacture, including, but not limited to, injection molding, or laser machining.

Each section 204 includes a housing 206 (FIGS. 4, 5) having opposing end portions 208, 210, and a penetrating portion 212 that extends from an end wall 214 at the end portion 210. In order to reduce manufacturing costs and complexity, each of the sections 204 may be formed as identical structures.

Figure 4:
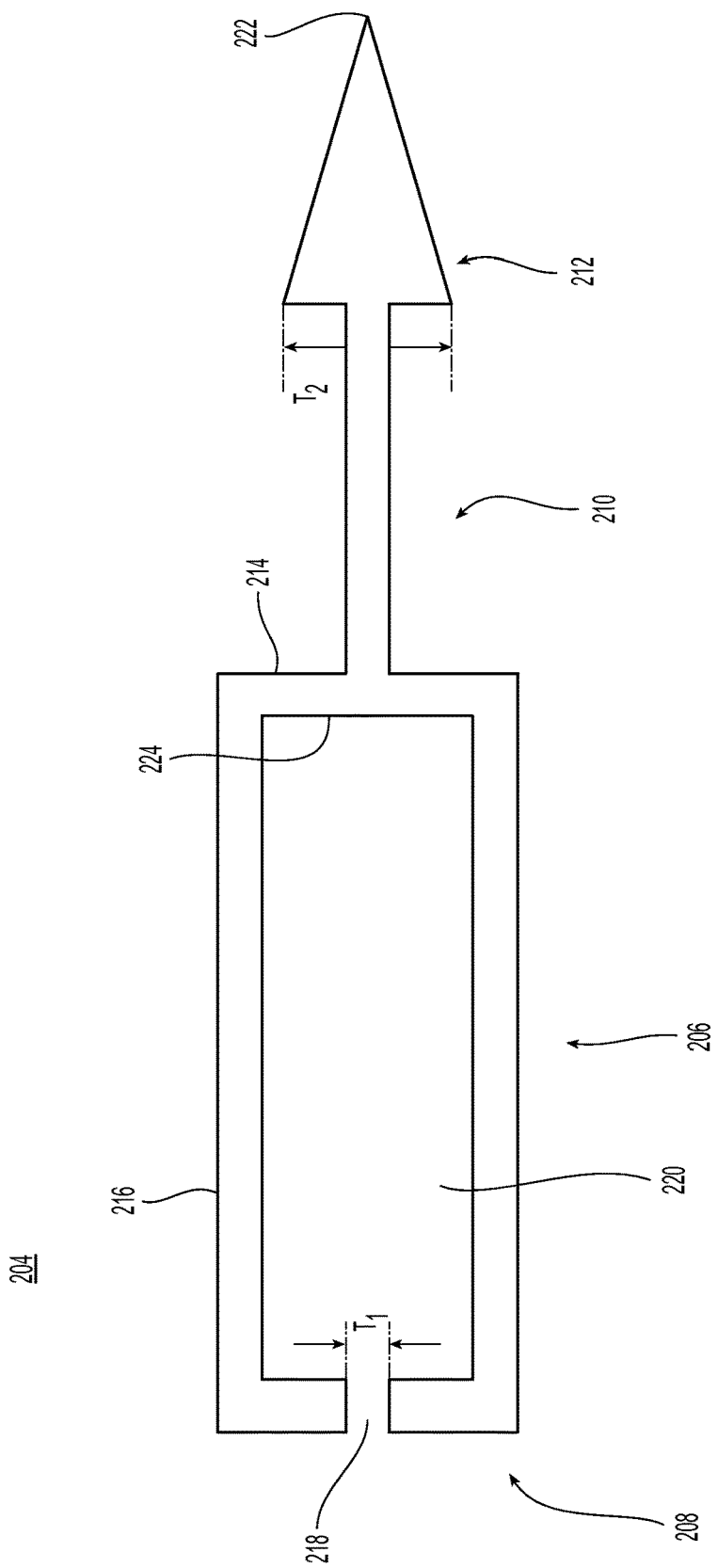
FIG. 4 is a longitudinal, cross-sectional view of one of the sections comprising the delivery member.

The housing 206 includes an outer wall 216 with an opening 218 formed in the end portion 208 that defines a transverse cross-sectional configuration "$T_1$" (FIG. 4). The outer wall 216 of each housing 206 defines an internal cavity 220 that is configured and dimensioned to accommodate the penetrating portion 212 of an adjacent section 204, as seen in FIG. 5.

The penetrating portion 212 defines a maximum transverse cross-sectional configuration "$T_2$" (FIG. 4) that is larger than the transverse cross-sectional configuration "$T_1$" defined by the opening 218, and includes a distal tip 222 that is configured and dimensioned to facilitate passage of the penetrating portion 212 through tissue, e.g., the tissue comprising the vessel wall W (FIG. 1) of the vessel V. To this end, the distal tip 222 of the penetrating portion 212 may include an incisive configuration, as illustrated in FIG. 4, for example. In alternate configurations of the delivery member 200, however, the distal tip 222 may include a more rounded, blunt configuration.

Figure 5:
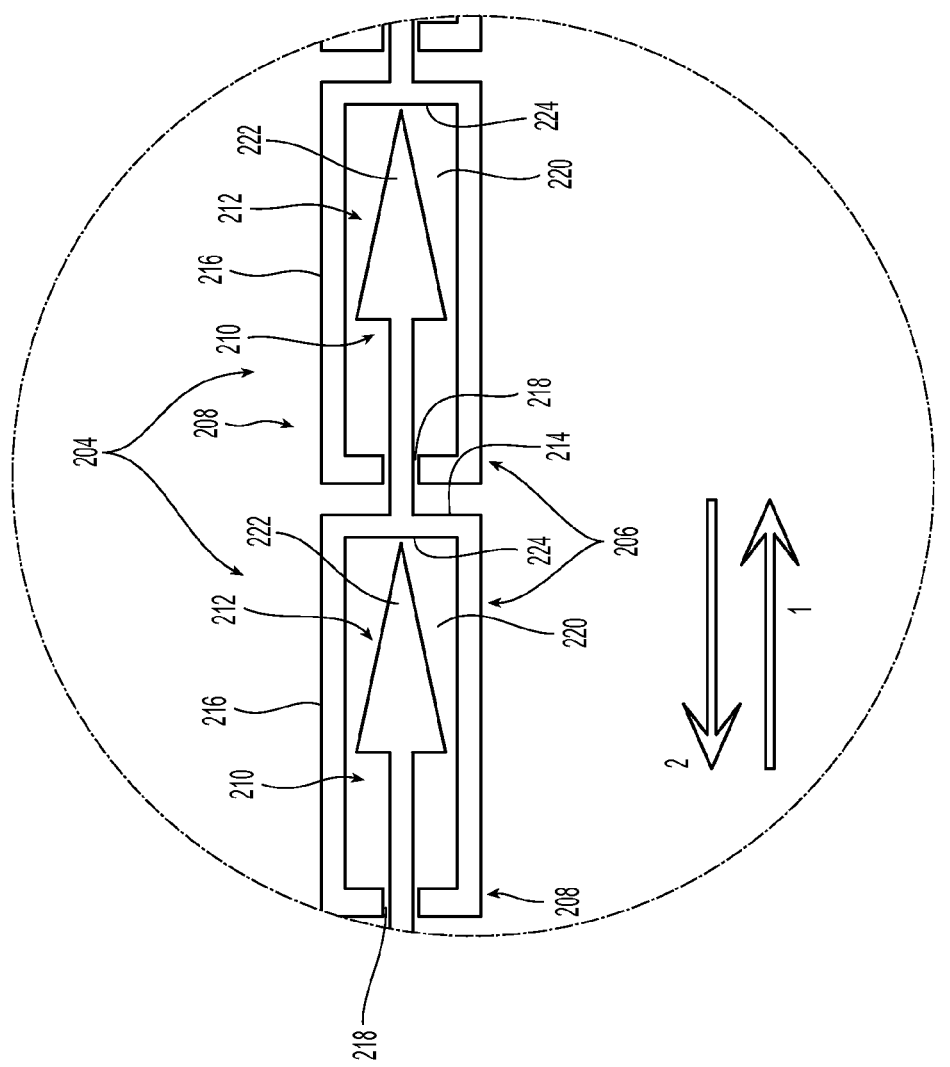
FIG. 5 is an enlargement of the area of detail identified in FIG. 2.
Figure 6:
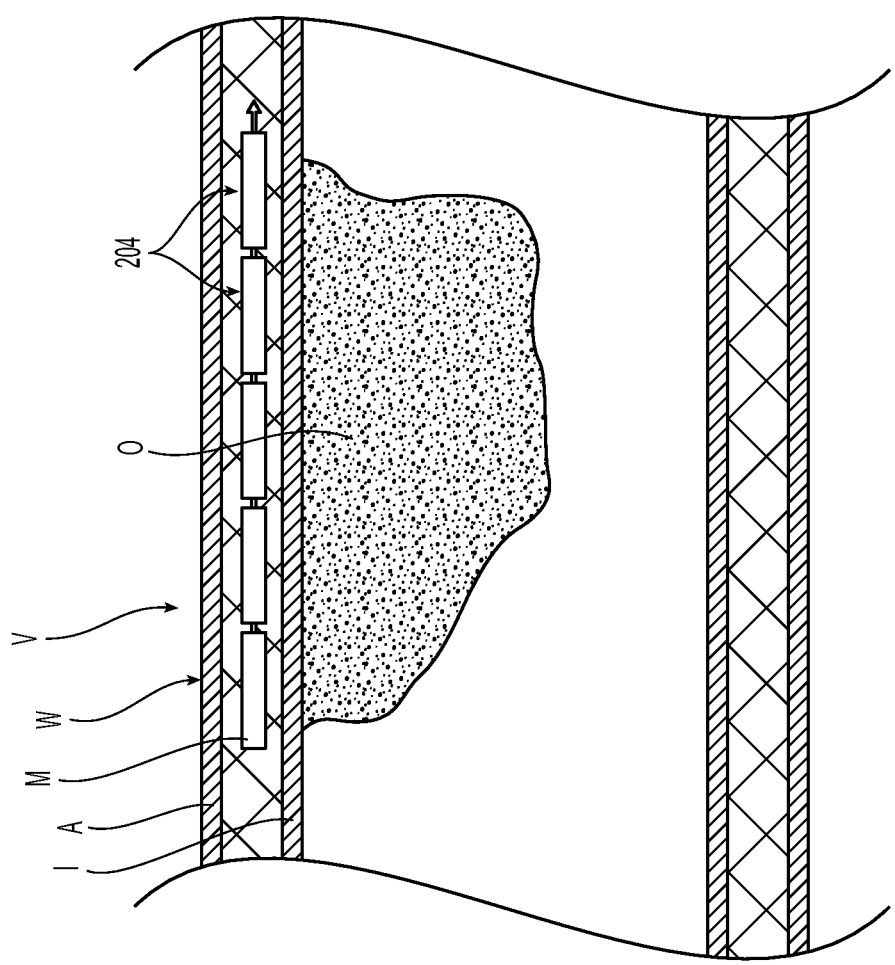
FIG. 6 is a partial longitudinal, cross-sectional view illustrating a portion of the delivery member deposited within the tissue of the blood vessel following withdrawal of the guide catheter.

Each of the sections 204 is configured and dimensioned to support and sustain a compressive load, e.g., a force applied in the direction of arrow 1 in FIG. 5, and yield to a tensile load, e.g., a force applied in the direction of arrow 2 in FIG. 5. With reference to FIG. 5, for example, upon the application of a compressive load to the delivery member 200, the end portion 210 of the housing 206 of one section 204 is forced into contact with the end portion 208 of the housing 206 of an adjacent section 204 such that the delivery member 2000 is advanced in the direction of the compressive load. Additionally, or alternatively, the applied compressive load may force the penetrating portion 212 of one section 204 into contact with an inner surface 224 of the internal cavity 220 of an adjacent section 204.

Upon the application of a tensile load to the delivery member 200, adjacent sections 204 are separated from each other. The applied tensile load causes the penetrating portion 212 of one section 204 to be withdrawn from the internal cavity 220 of an adjacent section 204 via resilient deformation of the penetrating portion 212 and/or the opening 218.

With reference now to FIGS. 1-6, an exemplary method of using the delivery member 200 includes positioning the guide catheter 100 adjacent the occlusion O in the vessel V, as illustrated in FIG. 3, and orienting the guide catheter 100 such that the port 108 is directed towards a desired point of entry into the vessel wall W. Dependent upon the particular requirements of the surgical procedure in which the system 1000 (FIG. 2) is used, and/or the nature of the occlusion O, either an antegrade approach or a retrograde approach may be employed in positioning the guide catheter 100.

Following placement of the guide catheter 100, the delivery member 200 is deployed through the port 108 (FIGS. 2, 3), and follows the natural dissection plane of the blood vessel V such that the delivery member 200 is passed through the intimal layer I into the medial layer M. During deployment of the delivery member 200, the guide catheter 100 remains in place to assist in stabilization of the delivery member 200.

Following entry into the medial layer M, the delivery member 200 is manipulated until the delivery member 200 spans the occlusion O such that at least one of the sections 204 comprising the body 202 of the delivery member 200 is positioned proximate each end $E_{O1}$, $E_{O2}$ of the occlusion O (FIG. 3). A tensile load is then applied to the delivery member 200 in order to separate adjacent sections 204 of the body 202. Specifically, since the drag force applied to the delivery member 200 by the tissue comprising the wall W of the vessel V is far greater than that applied by the guide catheter 100, the delivery member 200 will tend to separate adjacent the port 108, i.e., the point at which the drag force transitions, thereby allowing the clinician to control the number of sections 204 that are deposited within the tissue comprising the vessel wall W.

In order to increase the drag force applied to the delivery member 200 by the tissue comprising the wall W of the vessel V, one or more of the sections 204 of the delivery member 200 may include one or more surface irregularities. For example, in one embodiment, which is illustrated in FIG. 7, sections 204' are disclosed that include one or more barbs 205', each of which has a pointed apex $205_A'$. Alternatively, in another embodiment, which is illustrated in FIG. 8, sections 204" are disclosed that include one or more scales 205", each of which has a rounded end portion $205_A''$. The surface irregularities, e.g., the barbs 205' (FIG. 7) and/or the scales 205" (FIG. 8), may be either uniformly distributed across the outer surface of the sections 204', 204", as illustrated in FIGS. 7 and 8, or randomly distributed across the outer surface of the sections 204', 204".

To further facilitate separation of the sections 204, the guide catheter 100 may include a cutting or heating element (not shown) adjacent the port 108.

In order to facilitate proper orientation of the guide catheter 100 and/or deployment of the delivery member 200, the guide catheter 100 and/or the delivery member 200 may include radiopaque materials or portions, such as markers 226 (FIG. 2), which may be visualized under fluoroscopy.

Following deployment of the delivery member 200, and deposition of the sections 204 within the medial layer M, the aforementioned chemical agent is delivered. For example, the delivery member 200, e.g., the individual sections 204, may be formed from a non-biodegradable material, such as polyesters, e.g., polyalkyl terephthalates, polyamides, e.g., nylon, polyurethanes, polycarbonates, fluorooplymers, polyolefins, vinyl polymers, combinations thereof, and the like, and coated with the chemical agent, thereby permitting absorption of the chemical agent by the tissue comprising the medial layer M upon contact with the sections 204. During such delivery, since the delivery member 200 is initially concealed within the guide catheter 100, wash-off of the chemical agent is inhibited, as is dilution by the tissue. Alternatively, the delivery member 200, e.g., the individual sections 204, may be formed a biodegradable base material, into which the chemical agent may be incorporated. For example, the sections 204 may be formed from a base material including homopolymers, copolymers, and/or blends possessing glycolide, lactide, p-dioxanone, ε-caprolactone, trimethylene carbonate, orthoesters, phosphoesters, polysaccharides, modified starches, cellulose, oxidized cellulose, glycolide and lactide based polymers, such as poly-lactide-co-glycolide (PLGA) copolymers, and various combinations of the foregoing, and the chemical agent may be mixed into the base material during manufacture.

Following successful deployment of the sections 204, and delivery of the chemical agent, the guide catheter 100, as well as the remaining portion of the delivery member 200, can be retracted and withdrawn from the patient.

Figure 9:
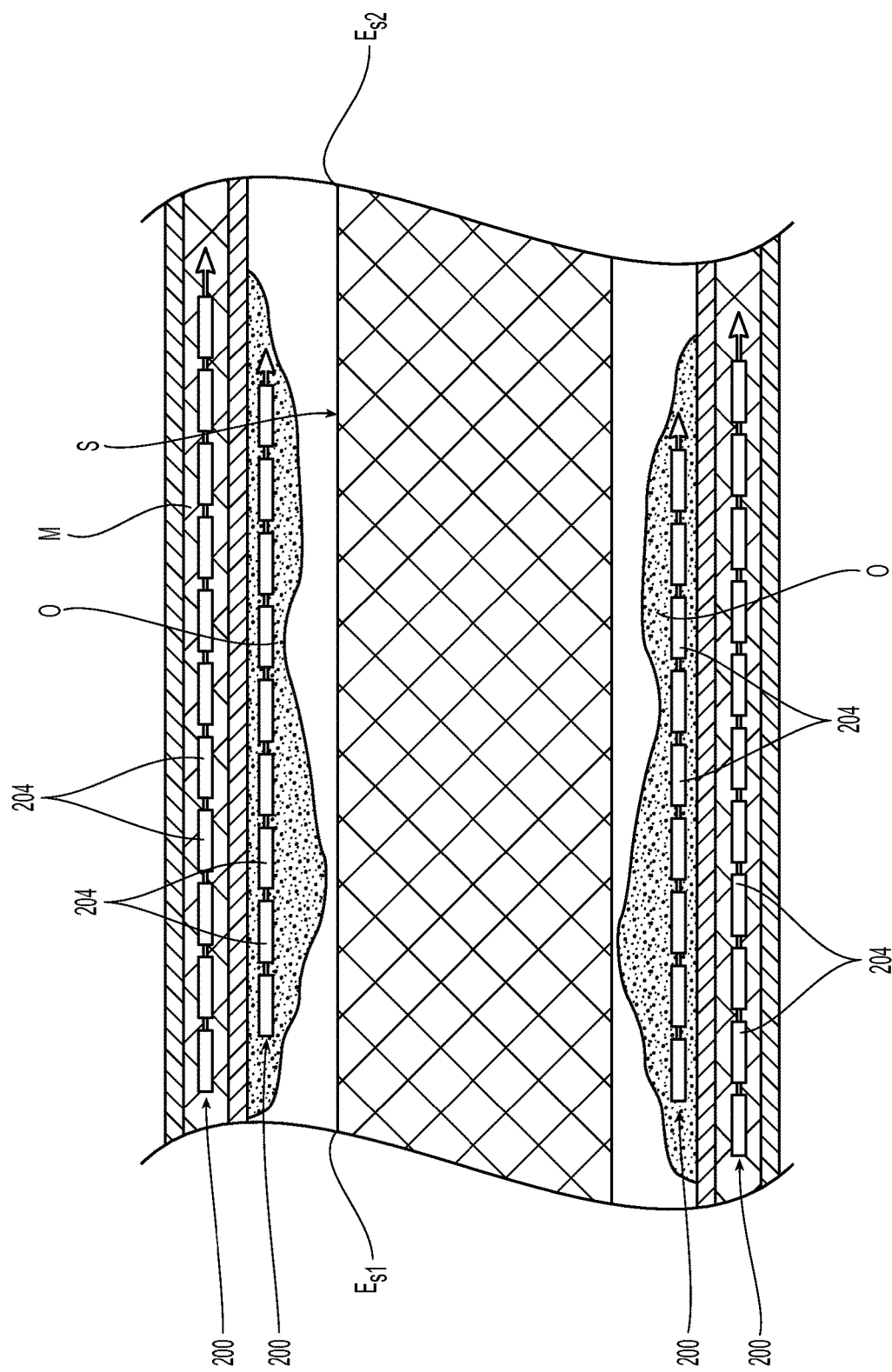
FIG. 9 is a partial longitudinal, cross-sectional view illustrating an alternate method of using the delivery member in conjunction with a stent.

The aforedescribed procedure may be used in conjunction with another surgical procedure, such as, for example, a procedure in which a thrombectomy catheter is employed to create an opening in the occlusion O (FIGS. 1, 9) in order to facilitate the placement of a stent S (FIG. 9). In such an application, the delivery member 200 may be inserted directly into, and deposited within, the tissue comprising the occlusion O. Additionally, or alternatively, through employ of the methodology discussed above, sections 204 of the delivery member 200 may be inserted into the medial layer M so as to span the stent S, i.e., such that at least one section 204 comprising the body 202 of the delivery member 200 is positioned proximate each end $E_{S1}$, $E_{S2}$ of the stent S.

Figure 10:
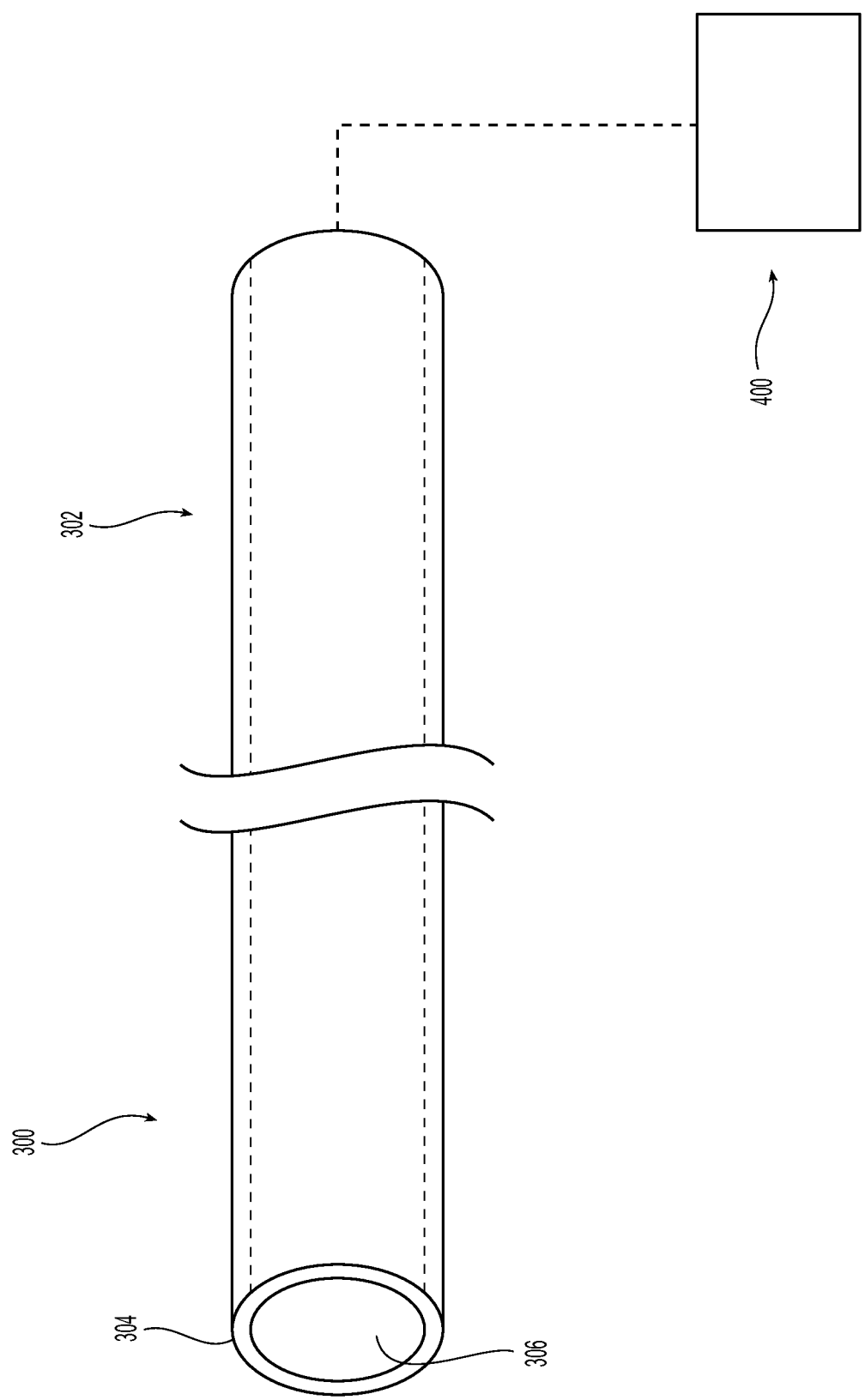
FIG. 10 illustrates an alternate embodiment of the delivery member shown in communication with a source including a chemical agent.

FIG. 10 illustrates an additional embodiment of the presently disclosed delivery member, which is identified by the reference character 300. The delivery member 300 includes a body 302 that is configured and dimensioned for insertion into, and movement through, the internal passageway 106 (FIG. 2) of the guide catheter 100. The body 302 includes an open distal end 304, and defines an internal channel 306.

In one method of using the delivery member 300, following placement of the guide catheter 100 within the vessel V, e.g., in the manner illustrated in FIG. 3, the delivery member 300 is deployed from the guide catheter 100, and passed through the intimal layer I into the medial layer M in the manner discussed above. Thereafter, the chemical agent is communicated into the internal channel 306 extending through the body 302 of the delivery member 300 from a source 400 (FIG. 10), such as a pump, syringe, or the like. The chemical agent is expelled through the open distal end 304 of the body 302, and delivered directly to the medial layer M.

Figure 11:
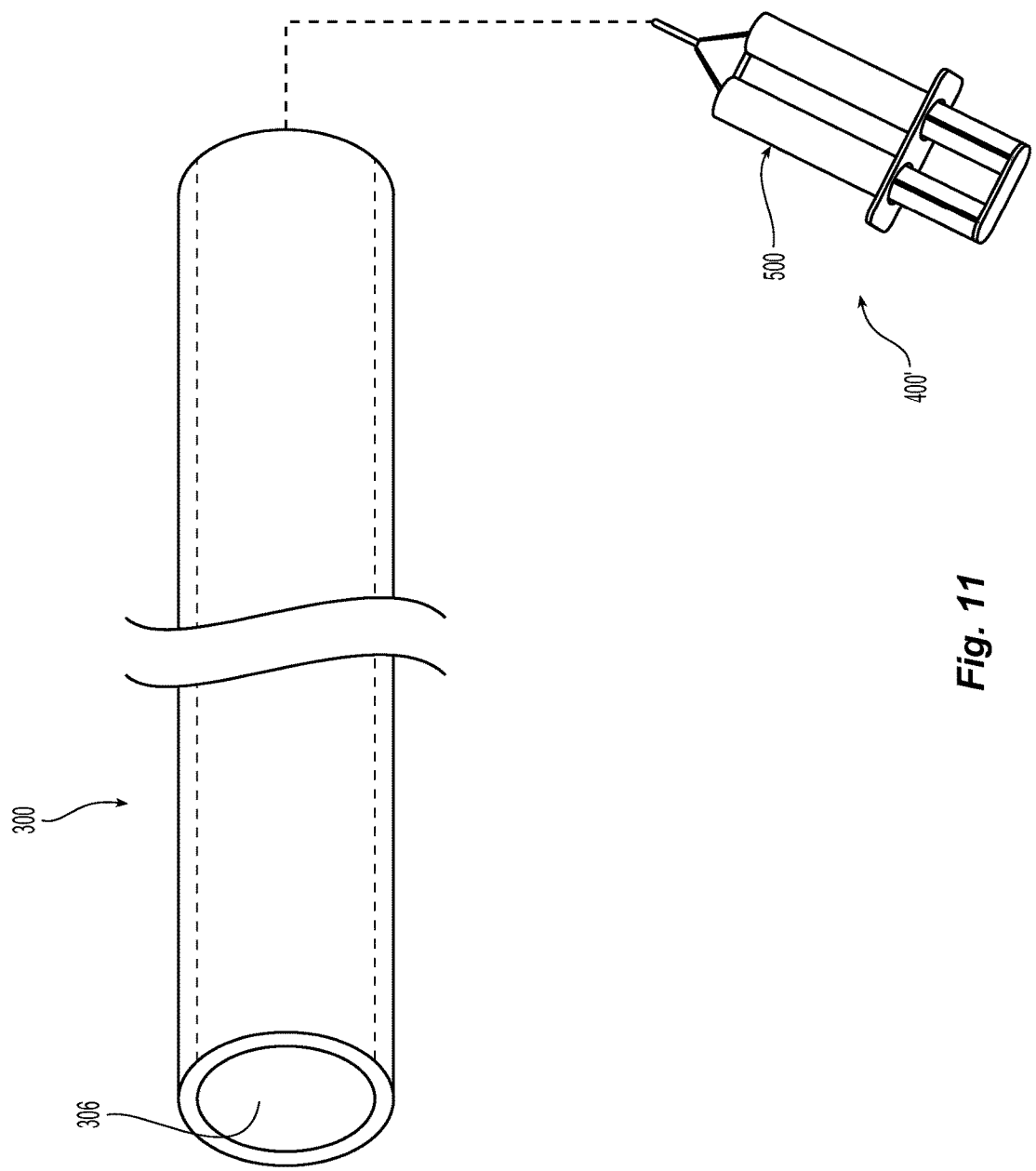
FIG. 11 illustrates the delivery member of FIG. 10, and an alternate embodiment of the source of the chemical agent.
Figure 12:
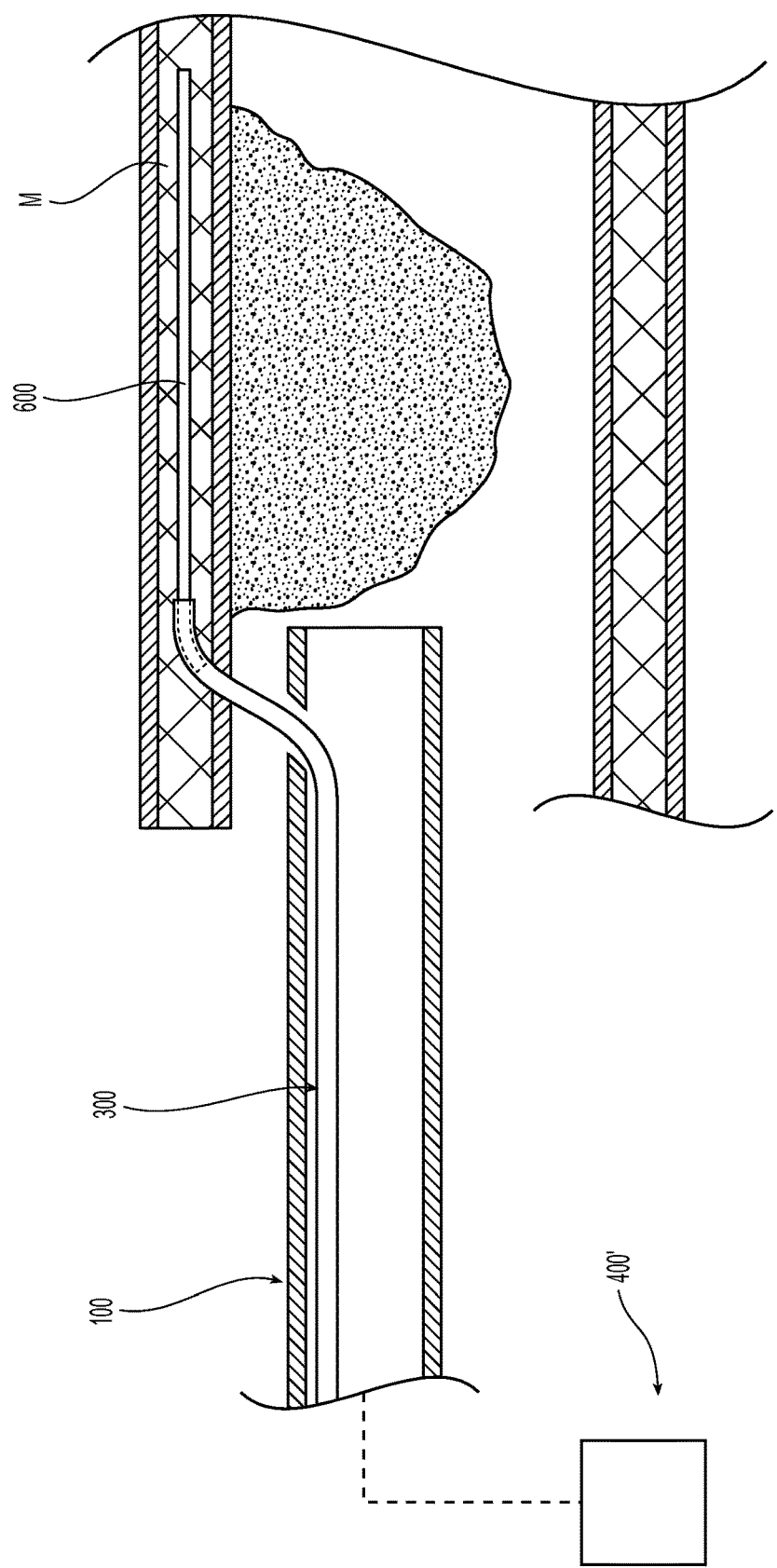
FIG. 12 is a partial longitudinal, cross-sectional view illustrating the delivery member of FIGS. 10 and 11 during the course of a surgical procedure in which a biodegradable filament is formed and deposited within the tissue of the blood vessel.

In an alternate method of using the delivery member 300, following deployment into the medial layer M, first and second compounds, one or both of which includes a chemical agent intended for delivery into the medial layer M, are delivered into the internal channel 306 extending through the body 302 from a source 400' (FIGS. 11, 12). For example, the first and second agents may include first and second hydrogel precursors, such as polymers, functional polymers, macromolecules, small molecules, or crosslinkers that can take part in a reaction to form a network of crosslinked molecules, e.g., a hydrogel. Although illustrated as a dual-barrel syringe 500 in FIG. 11, the source 400' may be any device suitable for the intended purpose of delivering first and second compounds, and maintaining separation of the first and second compounds until delivery.

Following discharge from the source 400', the first and second compounds combine and solidify to form a biodegradable filament 600 (FIG. 12) containing the chemical agent in situ, i.e., within the vessel wall W, and more particularly, within the medial layer M. The filament 600 can thus be extruded into the medial layer M from the delivery member 300, or alternatively, the filament 600 can be formed within the internal channel 306 extending through the body 302 of the delivery member 300, and the delivery member 300 can be withdrawn over the filament 600. In order to achieve delivery of the filament 600 in a desired manner, e.g., such that the filament 600 spans the occlusion O, the delivery member 300 can be manipulated within the medial layer M, e.g., advanced, retracted, and/or rotated.

In either method of use, after successful delivery of the chemical agent, the guide catheter 100, and the delivery member 300, can be retracted and withdrawn from the patient.

Figure 13:
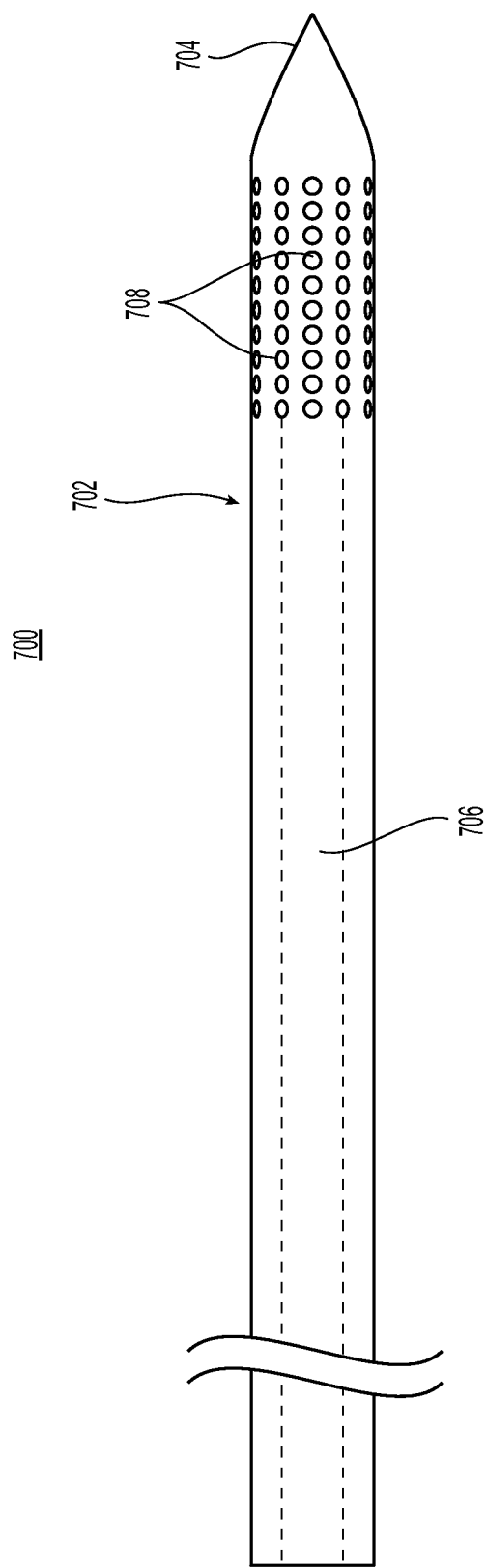
FIG. 13 illustrates an alternate embodiment of the delivery member of the present disclosure.
Figure 14:
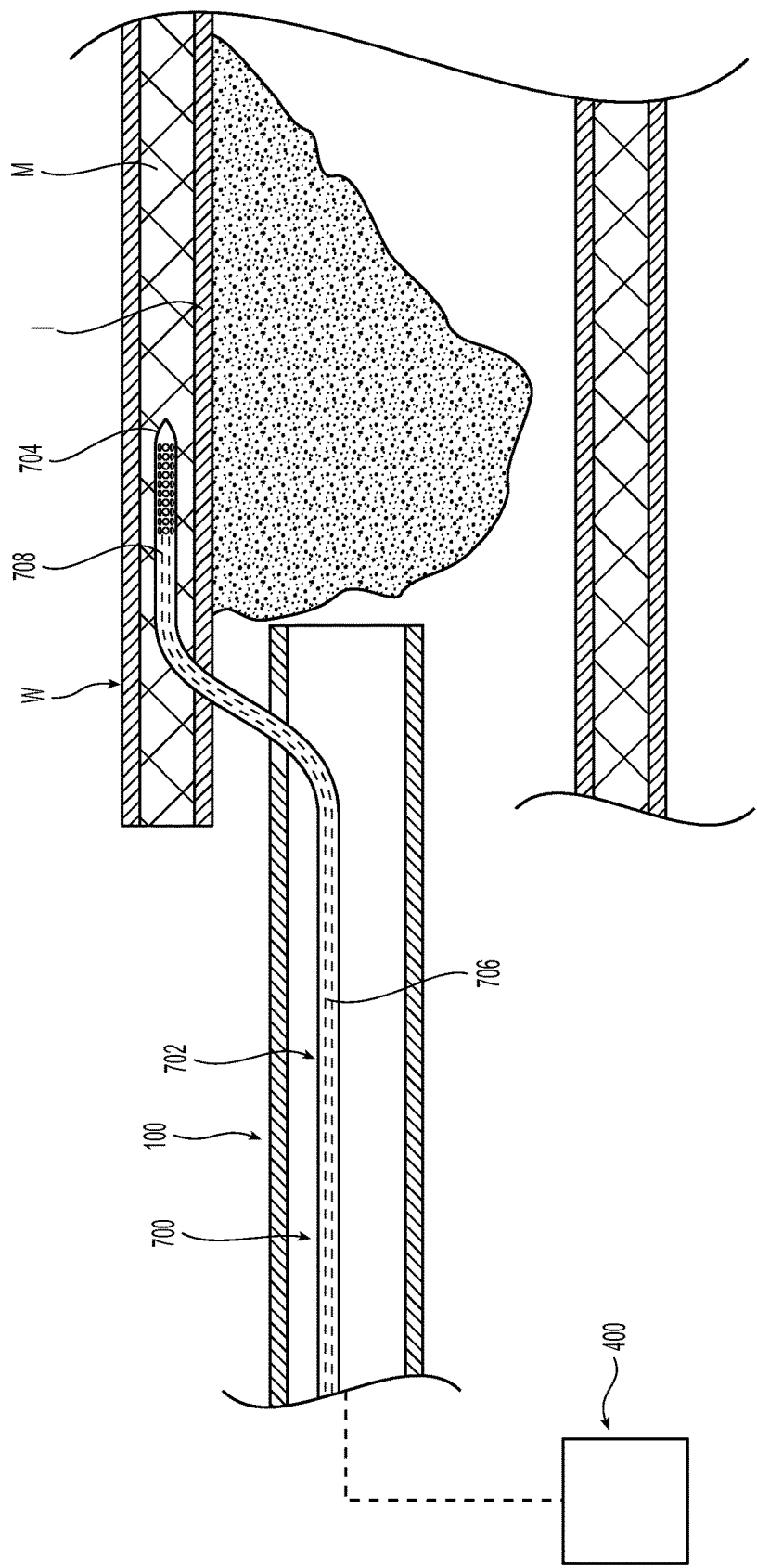
FIG. 14 is a partial longitudinal, cross-sectional view illustrating the delivery member of FIG. 13 positioned within the tissue of the blood vessel during the course of a surgical procedure.

FIGS. 13 and 14 illustrate another embodiment of the delivery member, which is identified by the reference character 700. The delivery member 700 is identical to the delivery member 300 (FIGS. 11, 12), but for the differences discussed below.

The delivery member 700 includes a body 702 having a closed distal end 704, and defining an internal channel 706. To facilitate advancement of the delivery member 700 through tissue, e.g., the tissue comprising the vessel wall W (FIG. 14), the closed distal end 704 of the body 702 may include a tapered configuration, as illustrated in FIGS. 13 and 14. The body 702 includes one or more radial openings 708, e.g., perforations, in communication with the internal channel 706 that permit the communication of fluid, such as the aforedescribed chemical agent(s), from the internal channel 706 externally of the delivery member 700.

During use of the delivery member 700, following placement of the guide catheter 100 in the manner discussed above, the delivery member 700 is deployed from the guide catheter 100, and passed through the intimal layer I into the medial layer M (FIG. 14). Thereafter, the chemical agent is communicated into the internal channel 706 extending through the body 702 of the delivery member 700, e.g., from the source 400. Upon communication into the internal channel 706, the chemical agent is expelled from the delivery member 700 through the radial opening(s) 708, and is delivered directly to the medial layer M. The delivery member 700 can be manipulated within the medial layer M, e.g., advanced, retracted, and/or rotated, to achieve delivery of the chemical agent to the any desired portion of the medial layer M.

Following successful delivery of the chemical agent, the guide catheter 100, and the delivery member 700, can be retracted and withdrawn from the patient.

Figure 15:
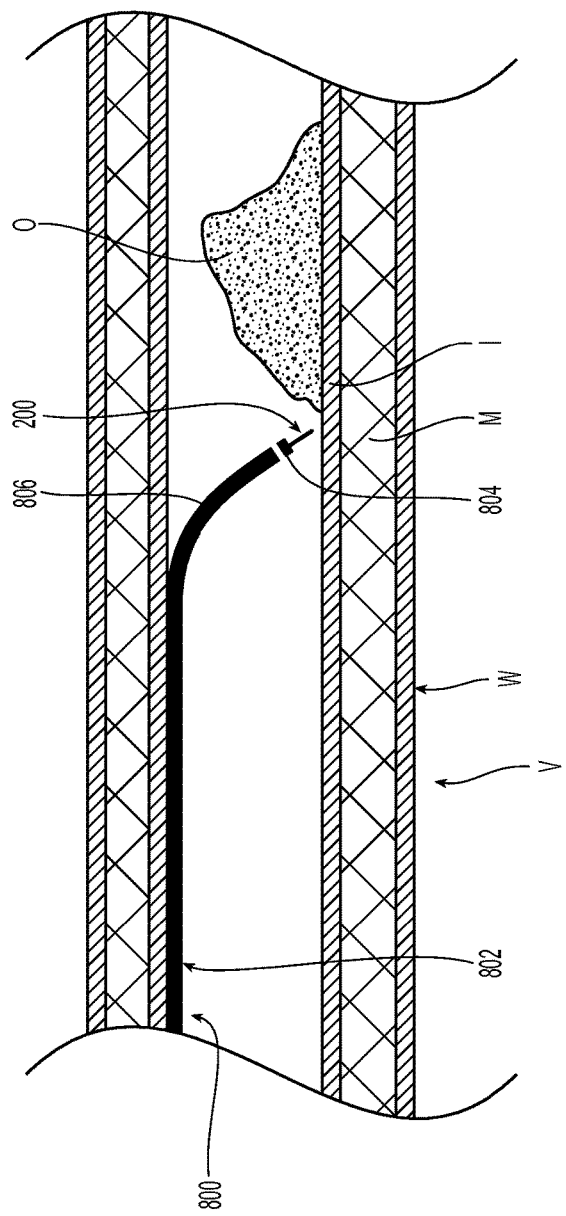
FIG. 15 is a partial longitudinal, cross-sectional view illustrating an alternate embodiment of the guide catheter during delivery of the delivery member.

In an additional embodiment of the disclosure, which is illustrated in FIG. 15, a guide catheter 800 is described for delivery of the delivery member, e.g., the delivery member 200 (FIG. 2). The guide catheter 800 includes a body 802 that facilitates directed delivery of the delivery member 200 through an open distal end 804 thereof via the incorporation of a bend 806.

Figure 16:
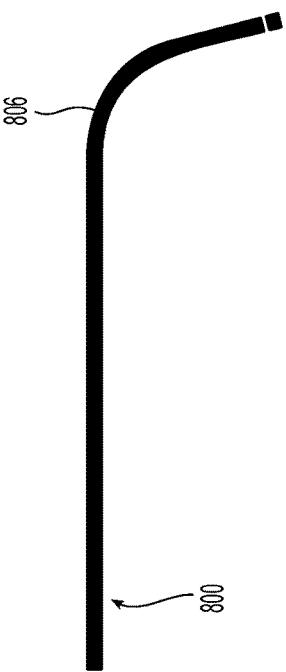
FIG. 16 is a side view illustrating an alternate embodiment of the guide catheter seen in FIG. 15.

It is envisioned that the guide catheter 800 may be configured and dimensioned to achieve any offset required by a particular procedure. For example, the bend 806 may achieve an offset of approximately 45°, as illustrated in FIG. 15, an offset of 75°, as illustrated in FIG. 16, or any other acute or obtuse angle required by the particular procedure in which the guide catheter 800 is employed, e.g., an offset of approximately 90°.

During use of the guide catheter 800, the guide catheter 800 is positioned within the vessel V such that the body 802 is positioned in contact with the wall W of the vessel, and the bend 808 is positioned approximately opposite the desired point of entry into the medial layer M. Thereafter, a delivery member, e.g., the delivery member 200 (FIGS. 2, 15), is inserted into the guide catheter 800, and the delivery member 200 is advanced through the distal end 804 of the guide catheter 800, through the intimal layer I, and into the medial layer M proximally of the occlusion O, as discussed above.

FIG. 17 illustrates another embodiment of the catheter, which is identified by the reference character 900. Whereas the guide catheter 800 is illustrated in FIGS. 15 and 16 as including a single bend, i.e., the bend 806, the guide catheter 900 includes multiple bends. For example, in the embodiment illustrated in FIG. 17, the guide catheter 900 includes a first bend 908 extending in a first direction, and a second bend 910 extending in a second, opposite direction to thereby collectively achieve an offset of approximately 90°.

Dependent upon the particular requirements of the procedure in which the guide catheter 900 is employed, the curvature of the bends 908, 910 may be varied, e.g., in direction and/or magnitude, to achieve any required degree of offset.

Additionally, or alternatively, it is envisioned that the guide catheter 900 may include a greater number of bends, e.g., three or four bends, to further adjust the offset of the guide catheter 900.

Persons skilled in the art will understand that the devices, systems, and methodologies specifically described herein, and shown in the accompanying drawings, constitute non-limiting, exemplary embodiments of the present disclosure, and that the elements and features shown or described in connection with one exemplary embodiment may be combined with those of another embodiment without departing from the scope of the present disclosure.

As well, those skilled in the art will appreciate further features and advantages of the presently disclosed subject matter based on the above-described embodiments and the claims. Accordingly, the present disclosure is not limited by what has been particularly shown and described.

The invention claimed is:

1. A delivery member configured to deliver a chemical agent to tissue, the delivery member comprising:
   a body including a plurality of discrete, separable sections comprising:
      a first section comprising:
         a first housing having a first opening formed therein and defining a first internal cavity; and
         a first penetrating member extending from the first housing; and
      a second section comprising:
         a second housing having a second opening formed therein and defining a second internal cavity; and
         a second penetrating member extending from the second housing,
      wherein each of the first and second penetrating members comprises a tip configured to facilitate passage of the delivery member through the tissue, and wherein the first penetrating member extends through the second opening and into the second internal cavity of the second housing; and
   the chemical agent, wherein the chemical agent is coated onto a surface of at least one section of the plurality of discrete, separable sections or incorporated within a material of the at least one section, such that the chemical agent is absorbable by tissue in contact with the at least one section.

2. The delivery member of claim 1, wherein the tip of each of the first and second penetrating members is incisive in configuration.

3. The delivery member of claim 1, wherein each section of the plurality of discrete, separable sections is identical in configuration.

4. The delivery member of claim 1, wherein the first and second housings each include first and second opposing ends, the first end including a respective one of the first opening or the second opening, the first and second penetrating members extending from the respective second end.

5. The delivery member of claim 1, wherein the plurality of discrete, separable sections is configured and dimensioned such that an applied tensile force separates adjacent sections.

6. The delivery member of claim 1, wherein the second opening in the second housing defines a transverse cross-sectional dimension smaller than a maximum transverse cross-sectional dimension defined by the first penetrating member.

7. The delivery member of claim 6, wherein the plurality of discrete, separable sections is configured and dimensioned such that an applied tensile force separates adjacent sections, and wherein the first and second sections are formed from a resilient material such that the tensile force applied to the delivery member causes at least one of the first penetrating member or the second opening in the second housing to deform, and thereby permit the first penetrating member to be withdrawn from the second housing to separate the first and second sections.

8. The delivery member of claim 7, wherein the plurality of sections further includes:
   a third section comprising a third housing having a third opening formed therein, and a third penetrating member extending from the third housing; and
   a fourth section comprising a fourth housing having a fourth opening formed therein, and a fourth penetrating member extending from the fourth housing.

9. The delivery member of claim 8, wherein the third penetrating member extends through the fourth opening and into the fourth internal cavity of the fourth housing.

10. The delivery member of claim 9, wherein the fourth opening in the fourth housing defines a transverse cross-sectional dimension smaller than a maximum transverse cross-sectional dimension defined by the third penetrating member.

11. The delivery member of claim 10, wherein the third and fourth sections are formed from a resilient material such that the tensile force applied to the delivery member causes at least one of the third penetrating member or the fourth opening to deform, and thereby permit the third penetrating member to be withdrawn from the fourth housing to separate the third and fourth sections.

12. A system for use in treating a blood vessel, the system comprising:
   a guide catheter insertable into a lumen of the blood vessel, the guide catheter defining an internal passageway;
   a delivery member insertable into the internal passageway of the guide catheter, the delivery member including a plurality of discrete, separable sections comprising:
   a first section comprising:
      a first housing having a first opening formed therein and defining a first internal cavity; and
      a first penetrating member extending from the first housing; and
   a second section comprising a second housing having a second opening formed therein and defining a second internal cavity; and
   a second penetrating member extending from the second housing,
   wherein each of the first and second penetrating members comprises a tip configured to facilitate passage of the delivery member through tissue comprising the blood vessel, and wherein the first penetrating member extends through the second opening and into the second internal cavity of the second housing; and
   a chemical anti-restenotic agent on at least one section of the plurality of discrete, separable sections, the chemical anti-restenotic agent being incorporated into a material from which the at least one section is formed or being positioned on the at least one section to enable absorption of the chemical anti-restenotic agent by tissue upon contact of the tissue with the at least one section.

13. The system of claim 12, wherein each section of the plurality of discrete, separable sections is identical in configuration.

14. The system of claim 12, wherein the plurality of discrete, separable sections is configured and dimensioned such that a tensile force applied to the delivery member separates adjacent sections.

15. The system of claim 12, wherein the second opening in the second housing defines a transverse cross-sectional dimension smaller than a maximum transverse cross-sectional dimension defined by the first penetrating member.

16. The system of claim 15, wherein the plurality of discrete, separable sections is configured and dimensioned such that a tensile force applied to the delivery member separates adjacent sections, and wherein the first and second sections are formed from a resilient material such that the tensile force applied to the delivery member causes at least one of the first penetrating member or the second opening in the second housing to deform, and thereby permit the first penetrating member to be withdrawn from the second housing to separate the first and second sections.

17. The system of claim 16, wherein the plurality of sections further includes:
   a third section comprising a third housing having a third opening formed therein, and a third penetrating member extending from the third housing; and
   a fourth section comprising a fourth housing having a fourth opening formed therein, and a fourth penetrating member extending from the fourth housing.

18. The system of claim 17, wherein the third penetrating member extends through the fourth opening and into the fourth internal cavity of the fourth housing.

19. The system of claim 18, wherein the fourth opening in the fourth housing defines a transverse cross-sectional dimension smaller than a maximum transverse cross-sectional dimension defined by the third penetrating member.

20. The system of claim 19, wherein the third and fourth sections are formed from a resilient material such that the tensile force applied to the delivery member causes at least one of the third penetrating member or the fourth opening the fourth housing to deform, and thereby permit the third penetrating member to be withdrawn from the fourth housing to separate the third and fourth sections.

21. A method of performing an endovascular procedure, the method comprising:
   inserting a guide catheter into a lumen of a blood vessel;
   advancing a delivery member through the guide catheter, wherein the delivery member comprises:
   a body including a plurality of discrete, separable sections comprising:
   a first section comprising:
      a first housing having a first opening formed therein and defining a first internal cavity; and
      a first penetrating member extending from the first housing; and
   a second section comprising:
      a second housing having a second opening formed therein and defining a second internal cavity; and a second penetrating member extending from the second housing, wherein each of the first and second penetrating members comprises a tip configured to facilitate passage of the delivery member through a tissue comprising a wall of the blood vessel, and wherein the first penetrating member extends through the second opening and into the second internal cavity of the second housing; and a chemical agent coated onto a surface of at least one section of the plurality of discrete, separable sections or incorporated within a material of the at least one section, such that the chemical agent is absorbable by tissue in contact with the at least one section; and deploying the delivery member from the guide catheter such that the delivery member is positioned between adjacent tissue layers forming the wall of the blood vessel; and delivering the chemical agent between the adjacent tissue layers forming the wall of the blood vessel.

22. The method of claim 21, wherein delivering the chemical agent includes depositing a portion of the delivery member between the adjacent tissue layers, and withdrawing a remaining portion of the delivery member from the blood vessel, the portion of the delivery member deposited between the adjacent tissue layers degrading over time, whereby the chemical agent is released into the tissue of the blood vessel.

23. The method of claim 22, wherein depositing the portion of the delivery member includes separating the first section from the second section.

24. The delivery member of claim 1, wherein the first and second housings each include first and second opposing ends, the first end defining respective ones of the first and second openings, and the first and second internal cavities extending substantially from the respective first end to the respective second end, and wherein the first and second penetrating members extend from the second end.

25. The delivery member of claim 1, wherein the chemical agent is coated onto the surface of the at least one section of the plurality of discrete, separable sections.

26. The delivery member of claim 1, wherein the chemical agent is incorporated within the material of the at least one section of the plurality of discrete, separable sections.

27. The delivery member of claim 1, wherein the at least one section is configured to degrade over time and release the chemical agent into the tissue in contact with the at least one section.

28. The system of claim 12, wherein the at least one section is configured to degrade over time and release the chemical anti-restenotic agent into the tissue in contact with the at least one section.

* * * * *